US00PP33785P2

(12) United States Plant Patent
Shreckhise

(10) Patent No.: US PP33,785 P2
(45) Date of Patent: Dec. 28, 2021

(54) ***THUJA* PLANT NAMED 'LILSHRECKTHU'**

(50) Latin Name: *Thuja occidentalis*
Varietal Denomination: LilShreckthu

(71) Applicant: Daniel K. Shreckhise, Mount Sidney, VA (US)

(72) Inventor: Daniel K. Shreckhise, Mount Sidney, VA (US)

( * ) Notice: Subject to any disclaimer, the term of this patent is extended or adjusted under 35 U.S.C. 154(b) by 0 days.

(21) Appl. No.: 17/137,467

(22) Filed: Dec. 30, 2020

(51) Int. Cl.
*A01H 5/12* (2018.01)
*A01H 7/00* (2006.01)

(52) U.S. Cl.
USPC ..... Plt./213
CPC ..... *A01H 7/00* (2013.01)

(58) Field of Classification Search
USPC ..... Plt./213
CPC ..... A01H 7/00
See application file for complete search history.

(56) References Cited

PUBLICATIONS

"Shrubs Vines Trees Evergreens Edibles" 2021 Star® Roses and Plants Catalog, published on Feb. 23, 2020, pp. 14 and 77.

*Primary Examiner* — Anne Marie Grunberg
(74) *Attorney, Agent, or Firm* — Panitch Schwarze Belisario & Nadel LLP; Stephany G. Small; Travis W. Bliss

(57) ABSTRACT

A new and distinct variety of *Thuja* plant, referred to by its cultivar name, 'LilShreckthu', is disclosed. The new variety forms attractive dark green colored foliage. The new variety provides moderately vigorous, upright, pyramidal and compact growth habit. The new variety is well suited for providing attractive ornamentation in the landscape.

1 Drawing Sheet

Botanical/commercial classification:
Latin name: *Thuja occidentalis.*
Varietal denomination: 'LilShreckthu'.

SUMMARY OF THE INVENTION

The new cultivar was discovered as a naturally occurring branch sport of the variety *Thuja occidentalis* 'Smaragd' (not patented) while growing in a controlled environment in Grottoes, Va. during Fall 1997.

It was found that the new variety of *Thuja* Plant of the present invention possesses the following combination of characteristics:

(a) forms dark green colored foliage, and
(b) provides moderately vigorous, upright, pyramidal and compact growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestor. More specifically, the 'Smaragd' variety (i.e., the branch sport parent) tends to provide multiple leaders, whereas the new variety favors a single leader, and the new variety is more compact compared to the 'Smaragd' variety. The new variety can be readily distinguished from related similar varieties. For example, the 'Degroot's Spire' variety (non-patented) grows to about twice the size of the plants of the new variety and exhibits a foliage arrangement that is more twisted compared to the new variety.

The new variety has been found to undergo asexual propagation by softwood cuttings. Asexual propagation by softwood cuttings in Cochranville, Pa. since November 2017 has shown that the characteristics of the new variety are stable and are strictly transmissible by such asexual propagation from one generation to another. Accordingly, the new variety undergoes asexual propagation in a true-to-type manner.

The new variety has been named 'LilShreckthu'.

The new variety was first offered for sale in the "SHRUBS VINES TREES EVERGREENS EDIBLES" 2021 *Star® Roses and Plants Catalog*, which was published on Feb. 23, 2020 by the inventor or by another who obtained the new variety directly or indirectly from the inventor. The first actual sale of the new variety was Jul. 16, 2020.

BRIEF DESCRIPTION OF THE PHOTOGRAPH

The accompanying photograph shows as nearly true as it is reasonably possible to make the same, in a color illustration of this character, a typical specimen of the plant of the new variety. Colors in the photograph differ slightly from the color values cited in the detailed description, which accurately describes the colors of 'LilShreckthu'. The plant depicted was approximately three years old and was growing in a 3-gallon container in Cochranville, Pa.

Drawing—illustrates a specimen of the plant displaying the overall growth habit—side view.

DETAILED BOTANICAL DESCRIPTION

The chart used in the identification of the colors is that of The Royal Horticultural Society (R.H.S. Colour Chart, 2001 edition), London, England. The terminology which precedes reference to the chart has been added to indicate the corresponding color in more common terms. The description is based on the observation of typical plants of the new variety at an age of approximately three years during the month of October while growing in a container in Cochranville, Pa. The growing conditions approximated those employed for the commercial production of *Thuja* plants.

Propagation:

*Type*.—Semi-hardwood cuttings.

Plant:

*Growth habit*.—Upright, pyramidal, compact.

*Form*.—Perennial evergreen shrub.

*Height*.—Approximately 85.0 cm on average in a three-gallon container.

*Width*.—Approximately 28.0 cm on average in a three-gallon container.

*Growth rate*.—Moderate.

*Root description*.—Fibrous.

*Root color*.—Commonly near Greyed-Orange Group 177A.

Stem:

*Shape*.—Oval.

*Size*.—Main branch: approximately 1.5 cm in diameter on average and approximately 85.0 cm in length on average. — lateral branches: approximately 3.0 mm in diameter on average and approximately 19.0 cm in length on average.

*Surface*.—Young branches are glabrous and knobby with scales.

*Color*.—New growth on sprays is commonly near Greyed-Orange Group 177B with scales near Greyed-Orange Group 177A, branches mature to near Brown Group 200C.

Branching:

*General*.—Main stem arises from base with numerous secondary branches, number of lateral branches, 19.0 cm in length, an average of 20 per main stem.

*Arrangement*.—Alternate.

*Aspect*.—Main stems upright, lateral stems held at about an average of 20-30 degree angle from the main stem with flat sprays that spread outwards.

*Internode length*.—Typically range from 1.0 cm at the base to 0.5 cm at the tip.

Foliage:

*Leaf arrangement*.—Numerous leaves arranged on planar branchlets (closely alternate or opposite), scale-like decussate.

*Leaf shape*.—Facial pair keeled, flat pair flattened and oblong.

*Leaf division*.—Simple.

*Leaf base*.—Cuneate.

*Leaf apex*.—Apiculate.

*Leaf venation*.—Not visible.

*Leaf margins*.—Entire; undulation is slight.

*Leaf surface*.—Upper and lower; glabrous, smooth, semi-glossy.

*Leaf glands*.—Inconspicuous.

*Leaf color*.—Young upper and lower surfaces: commonly near Green Group 141C. — mature upper and lower surfaces: commonly near Green Group 141A.

*Leaf size*.—Approximately of 2.0 mm in length on average and approximately 1.0 mm in width on average.

*Leaf quantity*.—About 8 leaves per cm in lateral branches.

*Fragrance*.—Somewhat acrid when crushed.

Development:

*Cold hardiness*.—USDA Zones 4 to 8.

*Flowers, cones, and seeds*.—None observed to date.

*Resistance to pests*.—No pest problems observed to date.

*Resistance to disease*.—No disease susceptibility observed to date.

The new variety, 'LilShreckthu', has not been observed under all possible environmental conditions to date. Accordingly, it is possible that the phenotypic expression may vary somewhat with changes in light intensity and duration, cultural practices, and other environmental conditions.

I claim:

1. A new and distinct cultivar of *Thuja* plant characterized by the following combination of characteristics:

(a) forms dark green colored foliage, and (b) provides moderately vigorous, upright, pyramidal and compact growth habit;

substantially as herein shown and described.

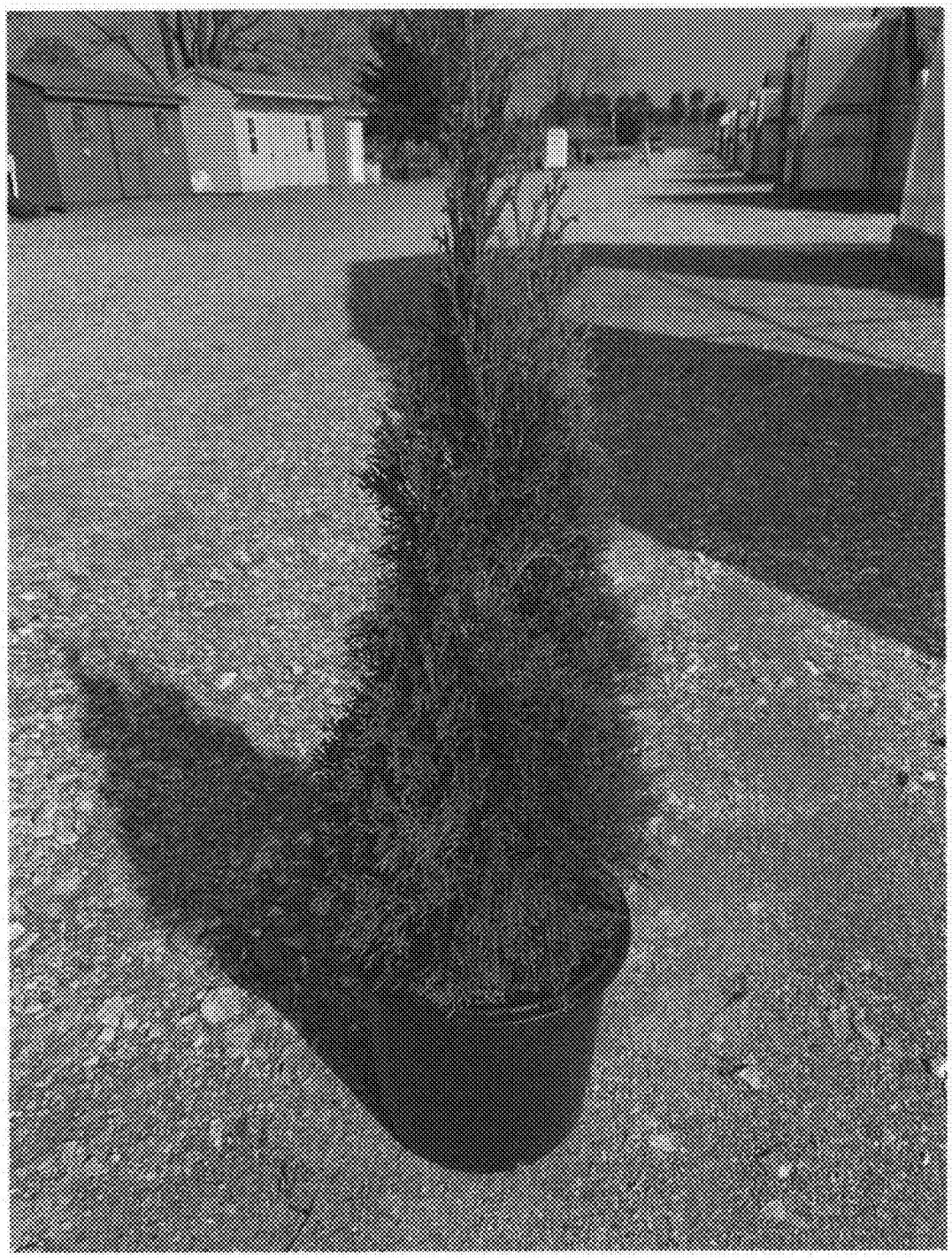

* * * * *